United States Patent
Shealy et al.

(10) Patent No.: US 7,365,154 B2
(45) Date of Patent: Apr. 29, 2008

(54) PEPTIDES ANTAGONISTIC TO AN ANTI-ANGIOGENIC ANTIBODY AND USES THEREFOR

(75) Inventors: David Shealy, Downingtown, PA (US); Sam Wu, Broomall, PA (US); Yan Chen, Wayne, PA (US); Audrey Baker, Philadelphia, PA (US)

(73) Assignee: Centocor, Inc., Malvern, PA (US)

( * ) Notice: Subject to any disclaimer, the term of this patent is extended or adjusted under 35 U.S.C. 154(b) by 406 days.

(21) Appl. No.: 10/873,848

(22) Filed: Jun. 22, 2004

(65) Prior Publication Data

US 2005/0084491 A1    Apr. 21, 2005

Related U.S. Application Data

(60) Provisional application No. 60/480,667, filed on Jun. 23, 2003.

(51) Int. Cl.
*A61K 38/04* (2006.01)
(52) U.S. Cl. ..................................... 530/327
(58) Field of Classification Search ................ None
See application file for complete search history.

(56) References Cited

U.S. PATENT DOCUMENTS

| 2003/6040044 | | 2/2003 | Giles-Komar |
| 2004/0185507 A1 | | 9/2004 | Giles-Komar |

FOREIGN PATENT DOCUMENTS

| CA | 2343602 | * 10/2001 |
| WO | WO 0212501 A2 | 2/2002 |
| WO | WO 02/31510 A1 | 4/2002 |

OTHER PUBLICATIONS

Van Regenmortel MHV. Mapping Epitope Structure and Activity: From One-Dimensional Prediction to Four-Dimensional Description of Antigenic Specificity Methods. 9(3):465-72, 1996.*
Reineke et al, "A synthetic mimic of a discontinuous binding site on interleukin-10", *Nature Biotechnology.*, 1999, pp. 271-275, vol. 17.
Birkenmeier et al, "Epitope mapping by screening of phage display libraries of a monoclonal antibody directed against the receptor binding domain of human alpha2-macroglobulin," FEBS lett. Oct. 20, 1997, vol. 416, No. 2, pp. 193-196.
Byun et al, Identification of the peptides that inhibit the function of human monoclonal thyroid-stimulating antibodies from phage-displayed peptide library. J. Clin Endocrinol Metaab. 2001. vol. 86, No. 7, pp. 33'11-3318.
Al-Bukhari et al, "An immuno-precipitation assay for determining specific interactions between antibodies and phage selected from random peptide expression libraries," J. Immunol. Methods, Jun. 1, 2002, Vo. 264, No. 1-2, pp. 163-171.

* cited by examiner

*Primary Examiner*—Maher M. Haddad
(74) *Attorney, Agent, or Firm*—Kenneth J. Dow

(57) ABSTRACT

The invention concerns antagonists of alphav-containing integrins which have therapeutic activity in oncology applications and methods for selecting such antagonists using a peptide which competes for alphaV-integrin binding with a known monoclonal antibody having demonstrated anti-tumor activity. The claimed peptide represents a conformational epitope or mimotope present on the ligand to which the therapeutic antibodies selectively bind.

3 Claims, 13 Drawing Sheets

FIG. 3A

```
                                 1                                                            60
H INTEGRIN ALPHA V NP_002201   (1) -----MAFPPRRRLRLGPRGLPLILSGLLLPLCR-----AFNLDVDSPAEYSGPEGSYF  (SEQ ID NO: 26)
HU INTEGRIN ALPHA 2B A34269    (1) -----MARALCPLQALWLLEWVLLLLGPCAAPPAWALNLDPVQLTFYAGPNGSQF    (SEQ ID NO:27)
HU INTEGRIN ALPHA5 NP_002196   (1) MGSRTPESPLHAVQLRWGPRRRPPLVPLLLLLVPPPRVGGFNLDAEAPAVLSGPPGSFF (SEQ ID NO:28)

61                                                          120
H INTEGRIN ALPHA V NP_002201  (50) GFAVDFFVPSASSRMFLLVGAPKANTTQPGIVEGGQVLKCDWSS-TRRCQPIEFDATGN-
HU INTEGRIN ALPHA 2B A34269   (51) GFSLDFHKDSHGR-VAIVVGAPRTLG--PSQEETGVFLCPWRAEGGQCPSLLFDLRDET
HU INTEGRIN ALPHA5 NP_002196  (61) GFSVEFYRPGTDG-VSVLVGAPKANTSQPGVLQGGAVYLCPWGASPTQCTPIEFDSKGSR 121                                                         180
H INTEGRIN ALPHA V NP_002201 (108) ------RDYAKDDPLEFKSHQWFGASVRSKQDKILACAPLYHWRTEMK---QEREPVGTC
HU INTEGRIN ALPHA 2B A34269  (108) ------RNVGSQTLQTFKARQGLGASVVSWSDVIVACAPWQHWNVLEKTEEAEKTPVGSC
HU INTEGRIN ALPHA5 NP_002196 (120) LLESSLSSEGEEPVEYKSLQWFGATVRAHGSSILACAPLYSWRTEKE---PLSDPVGTC 181                                                         240
H INTEGRIN ALPHA V NP_002201 (159) FLQDG--TKTVEYAPCRS---------QDIDADGQGFCQGGFSIDFTKADRVLLGGPSFY
HU INTEGRIN ALPHA 2B A34269  (162) FLAQPESGRRAEYSPCRGNTLSRIYVENDFSWDKRYCEAGFSSVVTQAGELVLGAPGGYY
HU INTEGRIN ALPHA5 NP_002196 (177) YLSTDNFTRILEYAPCRS---------DFSWAAGQGYCQGGFSAEFTKTGRVVLGGPSYF 241                                                         300
H INTEGRIN ALPHA V NP_002201 (209) WQGQLISDQVAEIVSKYDPNVYSIKYNN-QLATRTAQAIFDDSYLGYSVAVGDFNGDG-I
HU INTEGRIN ALPHA 2B A34269  (222) FLGLLAQAPVADIFSSYRPGILLMHVSSQSLSFDSSNPEYFDGYWGYSVAVGEFDGDLNT
HU INTEGRIN ALPHA5 NP_002196 (229) WQGQILSATQEQIAESYYPEYLINLVQG-QLQTRQASSIYDDSYLGYSVAVGEFSGDD-T 301                                                         360
H INTEGRIN ALPHA V NP_002201 (267) DDFVSGVPRAARTLGMVYIYDGKNMSSLYNFTGEQMAAYFGFSVAATDINGDDYADVFIG
HU INTEGRIN ALPHA 2B A34269  (282) TEYVVGAPTWSWTLGAVEILDSYYQRLHRLR-GEQMASYFGHSVAVTDVNGDGRHDLLVG
HU INTEGRIN ALPHA5 NP_002196 (287) EDFVAGVPKGNLTYGYVTILNGSDIRSLYNFSGEQMASYFGYAVAATDVNGDGLDDLLVG 361                                                         420
H INTEGRIN ALPHA V NP_002201 (327) APLFMDRGSDGKLQEVGQVSVSLQRAS---GDFQTTKLNGFEVFARFGSAIAPLGDLDQ
HU INTEGRIN ALPHA 2B A34269  (341) APLYMESRADRKLAEVGRVYLFLQPRGPH-ALGAPSLLLTGTQLYGRFGSAIAPLGDLDR
HU INTEGRIN ALPHA5 NP_002196 (347) APLLMDRTPDGRPQEVGRVVYYLQHPA--GIEPTPTLTLTGHDEFGRFGSSLTPLGDLDQ
```

FIG. 3B

```
                                        421                                                        480
H INTEGRIN ALPHA V NP_002201     (383)  DGFNDIAIAAPYGGEDKKGIVYIFNGRSTGLNAVPSQILEGQWAARSMPPSFGYSMKGAT
HU INTEGRIN ALPHA 2B A34269      (400)  DGYNDIAVAAPYGGPSGRGQVLVFLGQSEGLRSRPS---QVLDSPFPTGSAFGFSLRGAV
HU INTEGRIN ALPHA5 NP_002196     (405)  DGYNDVAIGAPFGGETQQGVVFVFPGGPGGLGSKPSQVLQPLWAASHTPDFFGSALRGGR 481                                                        540
H INTEGRIN ALPHA V NP_002201     (443)  DIDKNGYPDLIVGAFGVDRAILYRARPVITVNAGLEVYPSILNQDNKTCSLPGTALKVSC
HU INTEGRIN ALPHA 2B A34269      (457)  DIDDNGYPDLIVGAYGANQVAVYRAQPVVKASVQLLVQDSLN-PAVKSCVLPQTKTPVSC
HU INTEGRIN ALPHA5 NP_002196     (465)  DLDGNGYPDLIVGSFGVDKAVVYRGRPIVSASASLTIFPAMFNPEERSCSLE--GNPVAC 541                                                        600
H INTEGRIN ALPHA V NP_002201     (503)  FNVRFCLKADGKGVLPRKLNFQVELLLDKLKQKGAIRRALFLYSRSPSHSKNMTISRGGL
HU INTEGRIN ALPHA 2B A34269      (516)  FNIQMCVGATGHNIPQ-KLSLNAELQLDRQKPR-QGRRVLLLGSQQAGTTLNLDLGGKHS
HU INTEGRIN ALPHA5 NP_002196     (523)  INLSFCLNASGKHVAD-SIGFTVELQLDWQKQKGGVRRALFLASRQATLTQTLLIQNGAR 601                                                        660
H INTEGRIN ALPHA V NP_002201     (563)  MQCEELIAYLRDESEFRDKLTPITIFMEYRLDYRTAADTTGLQPILNQFTPANISRQAHI
HU INTEGRIN ALPHA 2B A34269      (574)  PICHTTMAFLRDEADFRDKLSPIVLSLNVSLPP----TEAGMAPAVVLHGDTHVQEQTRI
HU INTEGRIN ALPHA5 NP_002196     (582)  EDCREMKIYLRNESEFRDKLSPIHIALNFSLDPQAPVDSHGLRPALHYQSKSRIEDKAQI 661                                                        720
H INTEGRIN ALPHA V NP_002201     (623)  LLDCGEDNVCKPKLEVSDSDQKKIYIGDDNPLTLIVKAQNQGEG-AYEAELIVSIPLQA
HU INTEGRIN ALPHA 2B A34269      (630)  VLDCGEDDVCVPQLQLTASVTGSPLLVGADNVLELQMDAANEGEG-AYEAELAVHLPQGA
HU INTEGRIN ALPHA5 NP_002196     (642)  LLDCGEDNICVPDLQLEVFGEQNHVYLGDKNALNLTFHAQNVGEGGAYEAELRVTAPPEA 721                                                        780
H INTEGRIN ALPHA V NP_002201     (682)  DFIGVVRNNEALARLSCAFKTENQTRQVVCDLGNPMKAGTQLLAGLRFSVHQQSEMDTSV
HU INTEGRIN ALPHA 2B A34269      (689)  HYMRALSNVEGFERLICNQKKENETRVVLCELGNPMKKNAQIGIAMLVSVGNLEEAGESV
HU INTEGRIN ALPHA5 NP_002196     (702)  EYSGLVRHPGNFSSLSCDYFAVNQSRLLVCDLGNPMKAGASLWGGLRFTVPHLRDTKKTI 781                                                        840
H INTEGRIN ALPHA V NP_002201     (742)  KFDLQIQSSNLFDKVSPVVSHKVDLAVLAAVEIRGVSSPDHIFLPIPNWEHKENPETEED
HU INTEGRIN ALPHA 2B A34269      (749)  SFQLIQIRSKNSQNPNSKIVLLDVPVRAEAQVELRGNSFPASLVVAAEEGEREQN--SLDS
HU INTEGRIN ALPHA5 NP_002196     (762)  QFDFQILSKNLNNSQSDVVSFRLSVEAQAQVTLNGVSKPEAVLFPVSDWHPRDQPQKEED
```

FIG. 3C

```
                                      841                                                          900
H INTEGRIN ALPHA V NP_002201   (802)  VGPVVQHIYELRNNGPSSFSKAMLHLQWPYKYNNNTLLYILHYDIDGPMNCTSDMEINPL
HU INTEGRIN ALPHA 2B A34269    (807)  WGPKVEHTYELHNNGPTVNGLHLSIHLPGSQPSDLLYILDIQPQGGLQCFPQPPVNPL
HU INTEGRIN ALPHA5 NP_002196   (822)  LGPAVHHVYELINQGPSSISQGVLELSCPQALEGQQLLYTRVTG---LNCTTNHPINPK 901                                                          960
H INTEGRIN ALPHA V NP_002201   (862)  RIKISSLQT--TEKNDTVAGQGERDHLITKRDLALSEGDIHTLGCGVAQCLKIVCQVGRL
HU INTEGRIN ALPHA 2B A34269    (867)  KVDWGLPIPSPSPIHPAHHKRDRRQIFLPEPEQPSRLQDPVLVSCDSAPCTVVQCDLQEM
HU INTEGRIN ALPHA5 NP_002196   (879)  GLELDPEGS--LHHQQKREAPS-R--SSAS------SGPQILKCPEAECFRLRCELGPL 961                                                         1020
H INTEGRIN ALPHA V NP_002201   (920)  DRGKSAILYVKSLLWTETFMNKENQNHSYSLKSSASFNVIEFPYKNLPIEDITNSTLVTT
HU INTEGRIN ALPHA 2B A34269    (927)  ARGQRAMVTVLAFLWLPSLYQRPLD--QFVLQSHAWFNVSSLPYAVPPLSLPRGE--AQV
HU INTEGRIN ALPHA5 NP_002196   (927)  HQQESQSLQLHFRVWAKTFLQREHQ--PFSLQCEAVYKALKMPYRILPRQLPQKERQVAT 1021                                                         1080
H INTEGRIN ALPHA V NP_002201   (980)  NVTWGIQPAPMPVPVWVIILAVLAGLLLAVLVFVMYRMGFFKRVRPPQEEQEREQLQPH
HU INTEGRIN ALPHA 2B A34269    (983)  WTQLLRALEERAIPIWWVLVGVLGGLLLLTILVLAMWKVGFFKRNRPPLEEDDEEGE---
HU INTEGRIN ALPHA5 NP_002196   (985)  AVQWTKAEGSYGVPLWIIILAILFGLLLLGLLIYILYKLGFFKRSLPYGTAMEKAQLKPP

1081
H INTEGRIN ALPHA V NP_002201  (1040)  ENGEGNSET
HU INTEGRIN ALPHA 2B A34269   (1040)  ---------
HU INTEGRIN ALPHA5 NP_002196  (1045)  ATSDA----
```

PEPTIDES ANTAGONISTIC TO AN ANTI-ANGIOGENIC ANTIBODY AND USES THEREFOR

CROSS REFERENCE TO RELATED APPLICATION

This application is a non-provisional application filed under 37 CFR 1.53(b)(1), claiming priority under 35 USC 119(e) to provisional application No. 60/480,667 filed Jun. 23, 2003, the contents of which are incorporated herein by reference.

BACKGROUND OF THE INVENTION

1. Field of the Invention

The invention relates to methods of characterizing therapeutic antibodies and using information about binding specificity and more particularly as defined by a unique peptide ligand. The invention relates to therapeutic proteins which interact with alphaV containing integrin receptors.

2. Background of the Invention

Antibodies and T-cell receptor molecules possess variable regions that are responsible for specific antigenic recognition. The region of the antigen that is bound by the antibody or T-cell receptor is termed the antigenic determinant or epitope. Similarly, the variable regions of antibodies and T-cell receptors also contain determinants, or "idiotypes" that are immunogenic and are capable of initiating an anti-antibody response, an anti-idiotype ("anti-id") immune response.

More particularly, idiotopes are associated with the variable regions of antibodies and T-cell receptors. These variable regions confer antibody and T-cell receptor specificity for antigens. Idiotypes are immune system markers on antibodies and T-cell receptors. An idiotype is immunologically defined by reactivity with more than one anti-idiotypic antibody that recognizes an idiotypic determinant or idiotope within a given idiotype; therefore, an idiotype is made up of a collection of idiotopes.

Idiotopes are best defined by their binding to monoclonal anti-idiotypic antibodies. It also should be noted that idiotopes are distinct from isotypic (immunoglobulin class-specific), xenotypic (species specific) and allo-typic (certain population sub-group specific) determinants.

Each antibody and T-cell receptor has at least one paratope that is the binding site for an antigen determinant (the epitope). A paratope may serve as an idiotope, that is, the paratope may stimulate an anti-idiotypic response in which, like the original antigen, an anti-anti-idiotopic antibody binds to an epitope within the paratope. A subset of anti-paratope anti-idiotype ("anti-id") antibodies may mimic the immunologic properties of the original antigen and are known as "internal image" antibodies. In addition to the anti-paratopic anti-ids that mimic the original antigen, other anti-id antibodies define antibody and T-cell receptor idiotopes that also participate in the regulation of immune responses. These idiotypes are termed regulatory idiotypes and they are not necessarily "internal images" of the original antigen. For a general discussion of these background principles, see Burdette, S. and Schwartz, R., New Eng. J. of Med. 317:219 (1987).

Epitope mapping a monoclonal antibody or, in some cases, polyclonal serum, is generally understood to mean the process of deducing the exact region of the antigen or target molecule for which the antibody preparation has the highest affinity. A determinant or epitope of a target generally is understood to mean the portion of an antigen to which the most robust immune response is generated in terms of avidity and selectivity of binding. Peptides or other small fragments of an antigen can be used as immunogen (Niman et al. Proc. Natl. Acad. Sci. USA 1983, 80:4949-4951 and U.S. Pat. No. 5,030,565). In some cases peptides having unrelated sequences or structures can behave as epitopes or, mimotopes, in terms of being able to act as a binding partner for an antibody or compete for binding with the original antigen. Sequence analysis of these peptides can lead to identification of the structural and physicochemical features of the epitope. Systematic methods of altering peptide sequence and testing for antibody binding or competition between antigen and peptide have been used to perform epitope mapping. One such method, taught by Geysen et al. (Proc. Natl. Acad. Sci. USA 81: 3998-4001, 1984 and WO8403564) became widely used as it coupled the "pin" technology for solid phase peptide synthesis to ligand binding assays (sold as the Multipin Peptide Technology (Pep-Scan) by Chiron Mimotopes, San Diego, Calif.). In numerous cases, these epitopic peptides have little or no sequence homology with the original antigenic protein or peptide (Geysen et al. Mol. Immunol. 23: 709-715, 1986). This finding lent support to the concept that, in some cases, antibodies recognized "conformational epitopes" which are only formed in three-dimensional space upon folding and twisting of the linear sequence or because of association with another peptide as in heteromultimers. Conformational epitopes are also termed mimotopes. WO8600991A1 and WO8606487A1 teach methods of determining conformational epitopes.

Another widely used method for random generation of libraries of diverse peptides for studies is the use of bacteriophage expression systems or phage display. Phage display technology provides the additional advantage that the peptide or protein displayed on the coat protein of a bacteriophage is physically linked to its genetic constituents within the phage particle (Smith, Science 228: 1315-1317,1985). Such libraries have been used as the molecular biological equivalent of the Geyson method (Devlin et al. Science 1990, 249:404-406; Pluckthun, A. Curr. Op. Biotech. 1991, 2:238-246).

Therefore, the process of epitope mapping provides information about an antigenic molecule, which when linked to information about the biological activity of the antigen or properties altered in the presence of an antibody, provide a means to deduce or understand the biological functions of the target represented by an antigen or epitope and conversely the scope of the possible effects of an antagonistic antibody which prevents normal interaction of that epitope with its naturally occurring cognate ligands.

Directed biopharmaceutic drug design is highly desirable. Therefore, an understanding of protein-protein interactions and conformation specificity in target-substrate and target-ligand interactions is important. U.S. Pat. No. 6,143,876 teaches a method of obtaining antibodies to a specific epitopes of a complex which is only revealed upon formation of that complex. WO0170984 describes in detail the significance of understanding the surface epitope bound by a Mab specific for a protein involved in coagulation as the interaction with this factor, called tissue factor, which interacts with multiple ligands sequentially.

Integrins are a family of heterodimeric transmembrane receptors that mediate cell-cell and cell-extracellular matrix adhesion. Signal transduction by integrins has been shown to regulate diversified functions, including cell differentiation, proliferation, migration, apoptosis and angiogenesis (Shimizu et al., *Advances in Immunology* 72: 325-385,1999; Hynes, *Cell* 69: 11-25,1992). Alpha-V integrins comprise a subset sharing a common alpha-V subunit combined with 1 of 5 beta subunits (beta-1, -3, -5, -6, or -8. All or most alpha-V integrins recognize the sequence RGD in a variety of ligands (vitronectin, fibronectin, osteopontin, bone sialoprotein, thrombospondin, fibrinogen, von Willebrand factor, tenascin, and agrin) and, in the case of alphaVbeta8, laminin and type IV collagen. Blocking or inhibiting the processes associated with integrin signaling is therefore a logical approach to preventing, treating or limiting the spread of cancer in the body and other diseases such as those of the eye and cardiovascular system characterized by inappropriate angiogenesis or cellular adhesion and proliferation. Accordingly, applicants have discovered a monoclonal antibody that binds and blocks the activation of alphaV containing integrin receptors, which antibody is disclosed in copending application published as WO0212501.

Given the above mentioned value that epitope mapping provides, it can be seen that the discovery of any cognate ligand for a therapeutic antibody provides not only a novel mimotope that can function as an alternate directed antigen but further provide a significant tool to measure amount and function of that therapeutic antibody. The identification of ligands to CNTO95 mAb, by identifying antagonist peptides that can inhibit binding of CNTO95 to integrins $\alpha V\beta 3$ and $\alpha V\beta 5$, is one strategy for the discovery of such a composition.

SUMMARY OF THE INVENTION

The invention relates to a peptide of the formula:

Asp Phe $Xaa_1$ Ser $Xaa_2$ Trp $Xaa_3$ $Xaa_4$ $Xaa_5$ $Xaa_6$ $Xaa_7$ $Xaa_8$, wherein $Xaa_2$ is selected from Trp, Tyr and Phe, $Xaa_3$ is selected from Glu and Asp, $Xaa_4$ is selected Ile, Leu and Val and $Xaa_1$, $Xaa_5$ $Xaa_6$ $Xaa_7$ $Xaa_8$ are independently selected from any naturally occurring amino acid (SEQ. ID. NO: 1);

which peptide is a high affinity antagonist of an anti-alphaV integrin heterodimer antibody. More particularly, the peptide of the invention is a mimotope of CNTO95.

In one embodiment, the invention relates to a linear 12-mer peptide of the formula DFRSWWDLSGYR (SEQ. ID. NO: 2).

The peptides of the invention may be used as a method of therapeutically vaccinating a patient suffering from a disease characterized by angiogenic and metastatic processes.

The peptides of the invention may be used to immunize an animal for the purpose of generating a therapeutic antibody capable of treating or preventing diseases characterized by angiogenic and metastatic processes.

The peptides of the invention may be used in a method of screening for therapeutic or diagnostic antibodies that recognize a mimotope based on a structure formed in alphaV containing integrin receptors.

The peptides of the invention may be used in a method of selecting therapeutic anti-integrin molecules that bind the CNTO95 mimotope based on a structure formed in alphaV containing integrin receptors.

In another aspect, the invention relates to an isolated anti-integrin antibody which specifically binds at least one epitope comprising one or more, preferably 3 or more, of the amino acids of the peptide of SEQ. ID. NO: 1, other than the antibody designated CNTO 95 disclosed in published patent application WO0212501. In accordance with the invention, such antibody has at least one anti-integrin activity, including but not limited to inhibition of vitronectin binding, inhibition of binding of alpha V to at least one alpha V receptor or ligand, angiogenesis modulation or binding to integrin expressing cells. An antibody according to the invention includes any protein or peptide containing molecule that comprises at least a portion of an immunoglobulin molecule, such as but not limited to at least one complementarity determining region (CDR) of a heavy or light chain or a ligand binding portion thereof, a heavy chain or light chain variable region, a heavy chain or light chain constant region, a framework region, or any portion thereof, that can be incorporated into an antibody of the present invention.

An antibody of the invention can include or be derived from any mammal, such as but not limited to a human, a mouse, a rabbit, a rat, a rodent, a primate, or any combination thereof and includes isolated human, primate, rodent, mammalian, chimeric, humanized and/or CDR-grafted anti-integrin antibodies, immunoglobulins, cleavage products and other specified portions and variants thereof. The invention also relates to anti-integrin antibody compositions, encoding or complementary nucleic acids, vectors, host cells, compositions, formulations, devices, transgenic animals, transgenic plants, and methods of making and using thereof, as described herein together as combined with what is known in the art.

BRIEF DESCRIPTION OF THE DRAWINGS

FIG. 3A-C is a multiple alignment generated using ClustalW sequence of human alphaV (SEQ ID NO:26), alpha2B (SEQ ID NO:27), and alpha5 (SEQ ID NO:28) (GenBank Accession Nos: NP_002201, A34269, and NP_002196, respectively) with the D564-Q575 segment of the mature chain marked.

DETAILED DESCRIPTION OF THE INVENTION

Figure 1:
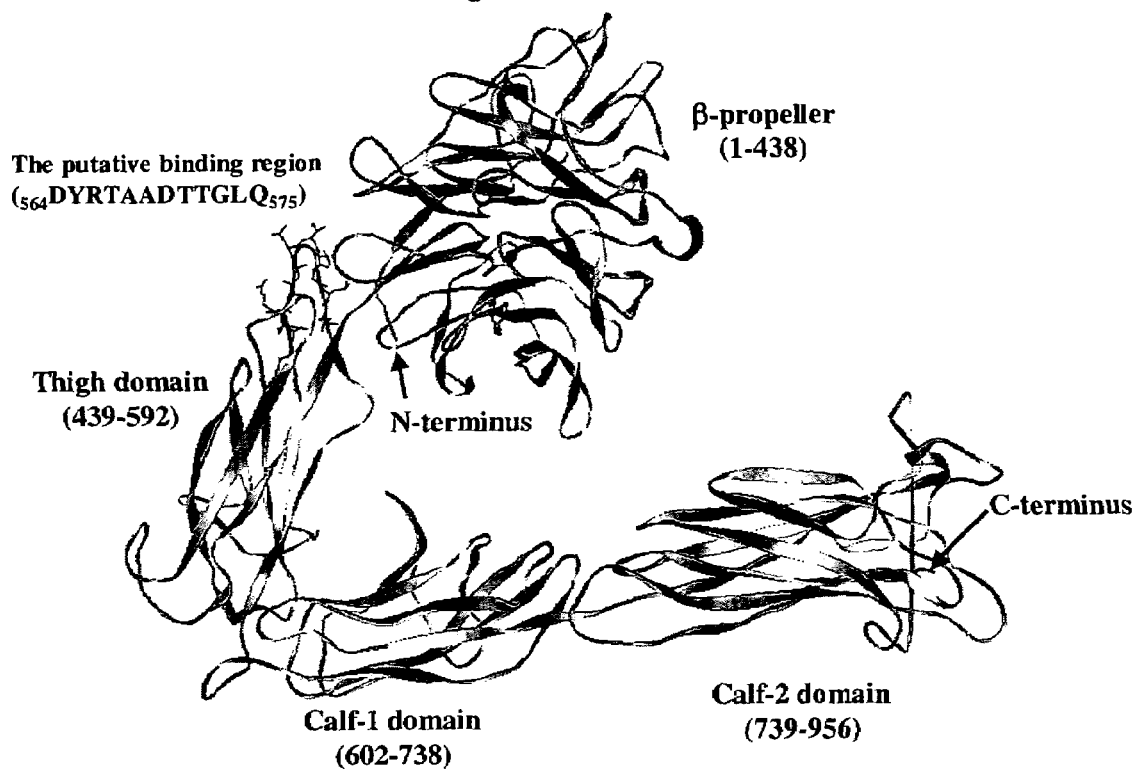
FIG. 1. is a graphic representation of the crystal structure of alphaV showing the position of D564-Q575 segment of the mature chain between the b-propeller and thigh structures.

Phage-displayed peptide libraries were used to identify novel ligands to the human monoclonal antibody, CNTO95. CNTO95 is a fully human IgG1, kappa monoclonal antibody produced at Centocor from a GenPharm transgenic mouse and has been shown to recognize integrins αVβ3 and αVβ5 in an EDTA-insensitive manner The CNTO95 anti-integrin antibody is disclosed in patent application WO0212501, hereby incorporated by reference into the present application.

Phage-displayed peptide libraries were probed in order to identify those peptides capable of preventing binding of Centocor monoclonal antibody, CNTO95, to its ligands, integrins αVβ3 and αVβ5. Screening of libraries of random 7-mers, 12-mers and cyclic 9-mers against CNTO95 identified such antagonist peptides. A linear 12-mer peptide, with the sequence DFRSWWDLSGYR (SEQ ID NO:2) (CEN2319), inhibits the interaction between CNTO95 and both integrin αVβ3 and αVβ5. Synthetic linear peptide CEN2319 was analyzed for CNTO95 binding activity using competitive enzyme-linked immunosorbent assays. The CNTO95 binding affinity of peptide CEN2319 was determined by this assay, giving EC50 value of 5.8 μM. From titration microcalorimetry analysis, peptide CEN2319 was shown to bind the CNTO95 with 2:1 stoichiometry and its binding affinity was 4.2 μM.

The biophysical properties of CEN2319 indicate that identification of small peptides presenting binding capacity to the monoclonal antibody CNTO95 are feasible and that such peptides can guide the discovery of other therapeutic agents specific for alphav-containing integrins. This peptide, which represents an antibody mimotope is a useful lead for the selecting of integrin receptor antagonist antibodies and peptides. In addition, these studies suggest strategies for mimicking binding sites on integrin receptors with phage displayed peptides.

The biophysical properties of CEN2319 as more generally indicated by the formula represented by SEQ. ID NO: 1 can be used to create other peptides which may, due to biological or chemical properties be advantageously used for the purposes of the invention. The substitution of amino acids of like properties is well known in the art and is termed conservative substitution. The twenty naturally occurring amino acids have been variously categorized into groups. These groups include amino acids with basic side chains (e.g., lysine, arginine, histidine), acidic side chains (e.g., aspartic acid, glutamic acid), uncharged polar or hydrophilic side chains (e.g., glycine, asparagine, glutamine, serine, threonine, tyrosine, cysteine), non-polar or hydrophobic side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

As stated above, in one aspect of the present invention, there is to an isolated anti-integrin antibody which specifically binds at least one epitope comprising one or more, preferably 3 or more, of the amino acids of the peptide of SEQ. ID. NO: 1, other than the antibody designated CNTO 95 disclosed in published patent application WO0212501. The antibody preferably further binds an alpha V integrin with an affinity ($K_d$) of at least $10^{-9}$ M, preferably at least $10^{-10}$ M, and/or substantially neutralize at least one activity of at least one alpha V integrin protein. In a preferred embodiment, the antibody binds an alpha V integrin protein with an affinity ($K_d$) of at least $1\times10^{-11}$ M, preferably $5\times10^{-11}$ M.

The present invention further provides, in one aspect, isolated nucleic acid molecules comprising, complementary, or hybridizing to, a polynucleotide encoding the aforementioned specific peptides or antibodies thereto, comprising at least one specified sequence, domain, portion or variant thereof. The present invention further provides recombinant vectors comprising said peptide or antibody encoding nucleic acid molecules, host cells containing such nucleic acids and/or recombinant vectors, as well as methods of making and/or using such nucleic acids, vectors and/or host cells. Thus, the invention comprises isolated nucleic acid encoding at least one isolated peptide of Seq. ID No. 1 or mammalian anti-integrin antibody which binds such peptide; an isolated nucleic acid vector comprising the isolated nucleic acid, and/or a prokaryotic or eukaryotic host cell comprising the isolated nucleic acid. The host cell can optionally be at least one selected from *E. Coli*, COS-1, COS-7, HEK293, BHK21, CHO, BSC-1, Hep G2, 653, SP2/0, 293, HeLa, myeloma, lymphoma, yeast, insect or plant cells, or any derivative, immortalized or transformed cell thereof. Also provided is a method for producing at least one peptide or antibody of the invention, comprising translating the peptide or antibody encoding nucleic acid under conditions in vitro, in vivo or in situ, such that the peptide or antibody is expressed in detectable or recoverable amounts.

The antibodies of this invention can be prepared in several ways well known in the art. In one aspect, the antibodies are conveniently obtained from hybridomas prepared by immunizing a mouse with the peptides of the invention. The antibodies can thus be obtained using any of the hybridoma techniques well known in the art, see, e.g., Ausubel, et al., ed., Current Protocols in Molecular Biology, John Wiley & Sons, Inc., NY, N.Y. (1987-2001); Sambrook, et al., Molecular Cloning: A Laboratory Manual, $2^{nd}$ Edition, Cold Spring Harbor, N.Y. (1989); Harlow and Lane, antibodies, a Laboratory Manual, Cold Spring Harbor, N.Y. (1989); Colligan, et al., eds., Current Protocols in Immunology, John Wiley & Sons, Inc., NY (1994-2001); Colligan et al., Current Protocols in Protein Science, John Wiley & Sons, NY, N.Y., (1997-2001), each entirely incorporated herein by reference.

Abbreviations

Abs antibodies, polyclonal or monoclonal aV integrin subunit alpha V b3 integrin subunit beta 3 b5 integrin subunit beta 5

Ig immunoglobulin

IgG immunoglobulin G

Mab monoclonal antibody.

While having described the invention in general terms, the embodiments of the invention will be further disclosed in the following examples.

EXAMPLE 1

Affinity Selection of Three Phage-Displayed Peptide Libraries on CNTO95

Affinity selection of phage-displayed peptide libraries was carried out. Three libraries, linear 7-mer, linear 12-mer and cyclic 9-mer, have been screened against CNTO95. One hundred μl of each phage library, at a concentration of about $5\times10^{10}$ pfu/ml in TBST buffer, was incubated in a microtiter well which was previously coated with 0.1 mg/ml of CNTO95 in 0.1M $NaHCO_3$ (pH 8.6) buffer. After incubation with constant rotation for 2 hours at 37° C. to facilitate the binding interaction, the wells were washed 10× with TBST buffer. The remaining bound phage were eluted with 100 μl of 0.1 mg/ml CNTO95, or 0.2 M Glycine-HCl (pH 2.2) and neutralized with 25 μl of 1 M Tris-base (pH 8.0). The eluted phages were propagated for use in the next affinity selection cycle. After three rounds of selection, an aliquot of eluted phage solution was plated onto a lawn of permissive E. coli ER2738 agar plates and colonies allowed to grow overnight at 37° C. Approximately 20 individual colonies were randomly selected and the sequence of the inserted peptide ligand was determined by DNA sequencing. The amino acid sequences of the phage-displayed peptides isolated by panning against CNTO95 are shown in Table 1.

TABLE 1

| | (eluted with 100 μg/ml CNTO95) | | | (eluted with 0.2 M Glycine-HCl, pH 2.2) | |
|---|---|---|---|---|---|
| Peptide | Sequence | Frequency* | Peptide | Sequence | Frequency |
| linear 12-mer | | | | | |
| 12p1 | DFRSWWDLSGYR (SEQ ID NO:2) | 14 (28) | 12pG1 | DFRSWWDLSGYR (SEQ ID NO:2) | 7 (8) |
| 12p2 | SKFQSYWELFPY (SEQ ID NO:6) | 8 (28) | 12pG2 | TH PNL SHAAQTR (SEQ ID NO:7) | 1 (8) |
| 12p3 | MPHKHEIWDWWY (SEQ ID NO:8) | 5 (28) | | | |
| 12p4 | STHLLPKPIMTN (SEQ ID NO:9) | 1 (28) | | | |
| linear 7-mer | | | | | |
| 7p1 | ALGHSFP (SEQ ID NO:10) | 9 (17) | 7pG1 | HSVYYPV (SEQ ID NO:11) | 5 (10) |
| 7p2 | SMERPFV (SEQ ID NO:12) | 4 (17) | 7pG2 | SHPASHD (SEQ ID NO:13) | 2 (10) |
| 7p3 | LPLTPLP (SEQ ID NO:14) | 2 (17) | 7pG3 | SMPPGLP (SEQ ID NO:15) | 1 (10) |
| 7p4 | MLTPPNP (SEQ ID NO:16) | 1 (17) | 7pG4 | ALGHSFP (SEQ ID NO:17) | 1 (10) |
| 7p5 | STTTAPR (SEQ ID NO:18) | 1 (17) | 7pG5 | SFVLPYY (SEQ ID NO:19) | 1 (10) |
| cyclic 9-mer | | | | | |
| C7Cp1 | CSPLFTPWC (SEQ ID NO:20) | 17 (17) | C7CpG1 | SPLFKPW (SEQ ID NO:21) | 9 (12) |
| | | | C7CpG2 | ESHSRPH (SEQ ID NO:22) | 2 (12) |
| | | | C7CpG3 | PQSEMDR (SEQ ID NO:23) | 1 (12) |

*Numbers in parentheses refer to the total number of plaques sequenced.

Within linear 12-mer group, there was an apparent preference (>58%) for the sequence of DFRSWWDLSGYR (SEQ ID NO:2). Within the cyclic-9 mer binders to CNTO95, the sequence of SPLFXPW (SEQ. ID. NO: 3) dominated in the randomly selected clones.

The linear 12-mer consensus peptide sequences has been aligned with sequences of the human integrin alpha subunits V, as well as beta subunit 3. The sequence alignment results were shown in Table 2, where matches are underlined with a solid line for exact identities and conservative substitutions with a dotted line.

TABLE 2

| | |
|---|---|
| Human alphaV | $_{561}$YRLDYRTAADTTGLQPILNQ$_{580}$ (SEQ ID NO:24) |
| Linear 12-mer | DFRSWWDLSGYR (SEQ ID NO:2) |
| Cyclic 9-mer | SPLFXPW (SEQ ID NO:3) |
| Human beta3 | $_{129}$VRQVEDYPVDIYYLMDLSYSMKDDL$_{153}$ (SEQ ID NO:25) |

TABLE 2-continued

| | |
|---|---|
| Linear 12-mer | DFRSWWDLSGYR (SEQ ID NO:2) |
| cyclic 9-mer | SPLFXPW (SEQ ID NO:3) |

Figure 2:
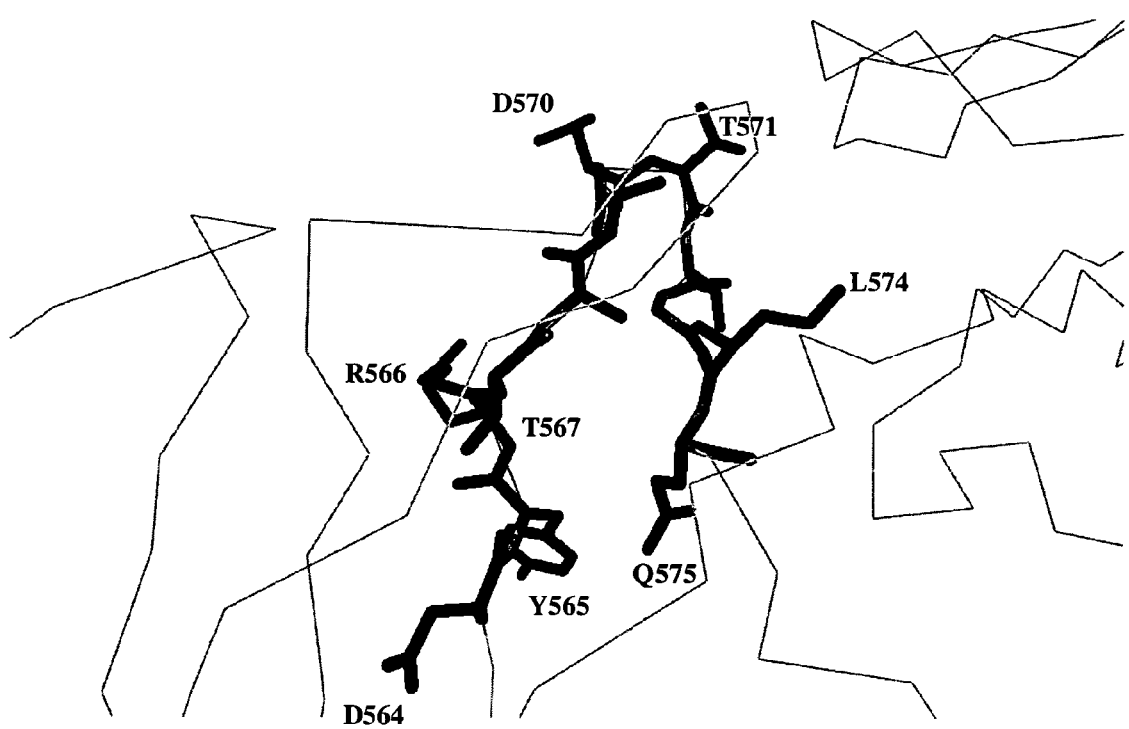
FIG. 2 is a graphic representation of the 3-dimensional spatial positioning of the D564-Q575 segment of the mature chain.

After comparing the peptide sequences to the extracellular segments of integrin αVβ3, it was found that among the possible matches or regions with close homology the 12 residue segment D564-Q575 of the mature chain of αV was the closest match of surface-exposed segments. There was little or no homology to any surface exposed region of the beta subunits. This analysis was based on the crystal structure of a soluble form of αVβ3 published by Xiong et al. (Science 294: 339-345, 2001 and Science 296: 151-155, 2002) shown in FIG. 1. The region forms a loop protruding from the Thigh (439-592) domain towards the beta-propeller (1-438) (FIG. 2). A multiple sequence alignment of alphaII, alpha5, and alphaV show this to be the region of least homology between the species, indicating that this domain is unique to the alphaV integrin family and a good candidate for a subunit specific epitope (FIG. 3B).

Based on this analysis, two synthetic peptides, CEN 2319 (DFRSWWDLSGYR, consensus sequence selected out from linear 12-mer peptide library) (SEQ ID NO:2) and CEN2322 ($_{564}$DYRTA ADTTGLQ$_{575}$, sequence of αV) (SEQ. ID. NO: 4) were synthesized and examined for their binding affinities by competition ELISA for further validation. The peptide, SPLFXPW (SEQ. ID. NO: 3 ) (flanked by cysteine residues which form a disulfide bond), was also tested for binding to CNTO95 using the ELISA format but no specific binding was detected.

EXAMPLE 2

Elisa for CNTO95 Binding to Synthetic Peptides

Figure 4A:
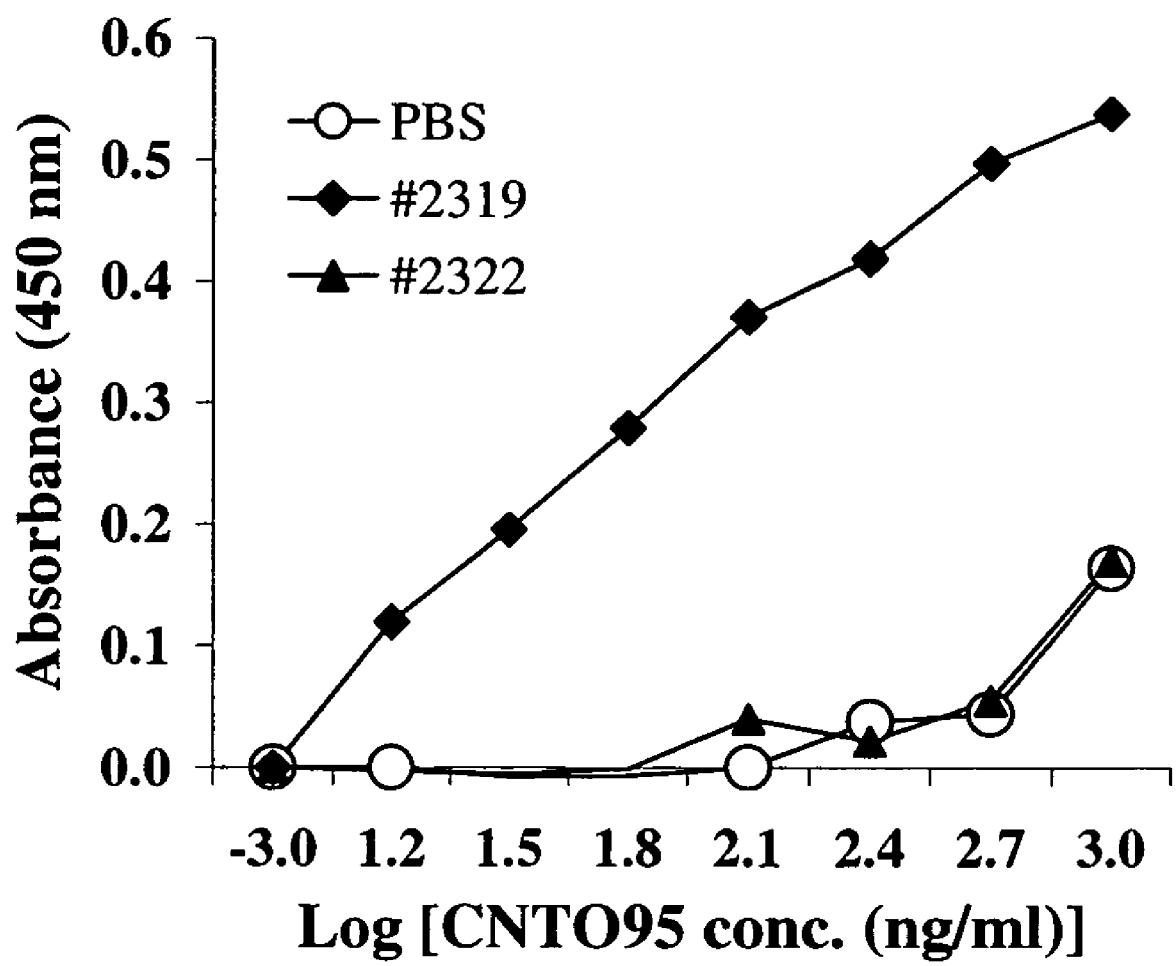
FIG. 4 contains graphs showing the results of ELISA assays demonstrating the concentration dependence of CNTO95 mAb binding to synthetic peptide-coated microwell plates: CEN2319 (mimotipe) and CEN2322 (alphaV segment) (A); direct comparison of CNTO95 binding, an anti-alphaVbeta3 Mab (LM609) and an anti alphaVbeta5 Mab (PIF6) to CEN2319 coated plates (B); and results of ELISAs for CNTO1275 mAb binding to synthetic peptides (C).
Figure 4B:
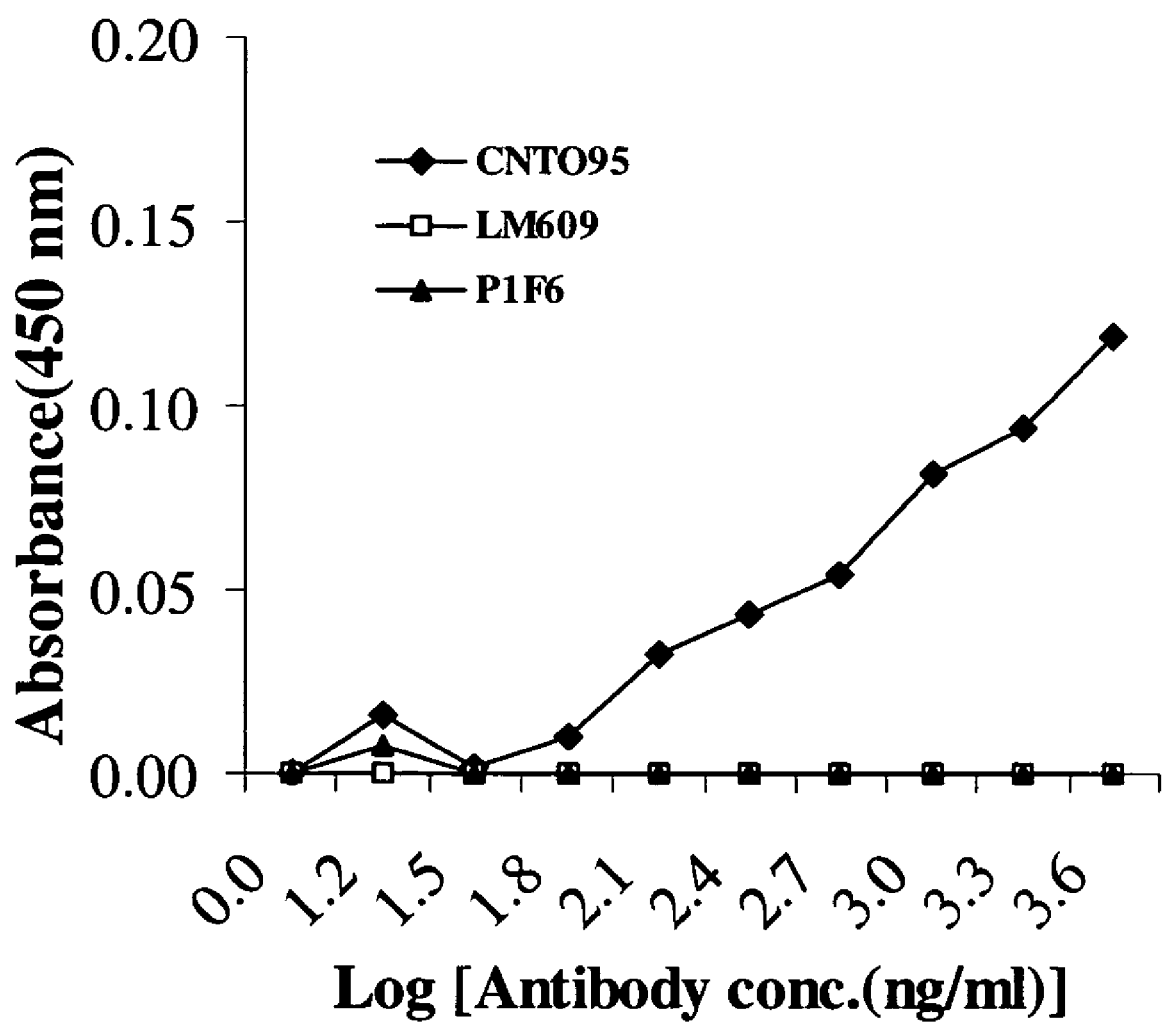
Figure 4C:
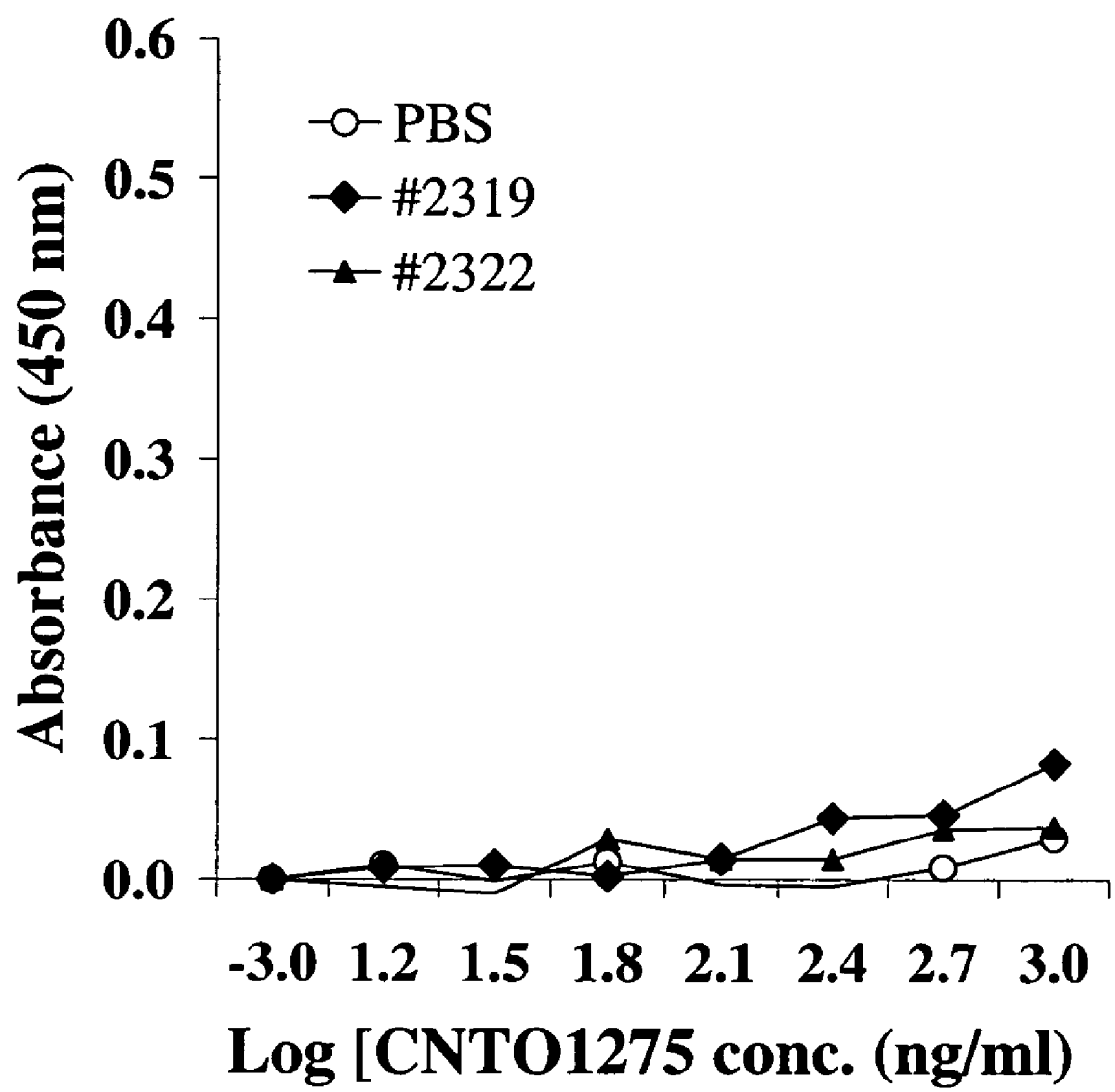

To verify the binding activity of synthetic peptides to CNTO95 mAb, ELISAs were performed using peptide-coated plates. PRO-Bind ELISA plates (Falcon) were coated with 100 µl (100 µg/ml) of either CEN 2319, CEN2322 or PBS buffer. Peptide-charged ELISA plates were incubated with 100 µl of various concentrations of CNTO95 mAb for 2 hours at 37° C., and the wells then were washed with PBS plus 0.5% Tween 20 (PBST). Binding was detected with a 1:5,000 dilution of of peroxidase-conjugated goat anti-human IgG, Fc gamma fragment antibody (Jackson) and color development with 3,3',5,5'-tetramethyl-benzidine dihydrochloride (TMB). The reaction was detected by reading the absorbance at 450 nm. PBS-coated wells were used as background control. The results showed that synthetic peptide CEN2319 could be recognized specifically by mAb CNTO95 (FIG. 4A). In contrast, commercially available antibodies to alphaVbeta3, LM609 (Chemicon, Temacula, Calif.) and to alphaVbeta5, PIF6 (GIBCO, Gaithersburg, Md.) did not bind the CEN2319 coated plates (FIG. 4B). Another set of negative control was performed using mAb CNTO1275 (FIG. 4C). The binding signal is negative.

Conclusion: CEN2319 indeed shows specific binding to CNTO95 (FIG. 4A) but not to other antibodies recognizing alphaV-containing integrins (FIG. 4B) and not to another human mAb to an unrelated antigen, CNTO1275 (FIG. 4C). The non-binding antibodies, clone LM609 and P1F6, have been previously shown not to compete with CNTO95 (WO0212501). Therefore, the peptide CEN2319 binding assays support that the epitope bound by CNTO95 is distinct from other integrin binding Mabs. A peptide (CEN2322) made from an actual sequence segment of alphaV also did not bind to CNTO95 (FIG. 4B) indicating that a unique non-linear epitope is recognized by CNTO95.

EXAMPLE 3

Evaluation of Binding Specificity for CEN2319 Peptide to CNTO95

Competitive ELISA on microtiter plates coated with integrins αVβ3 or αVβ5 were carried out to evaluate the binding specificity for CEN2319 peptide to CNTO95 mAb. 100 ul of 5 µg/ml either αVβ3 or αVβ5 (Chemicon, Temacula, Calif.) was coated on the ELISA plates at 40° C. over night. Then, 100 µl of 2 µg/ml CNTO95 was pre-incubated at room temperature for 30 minutes with various concentration peptides (100 µl), ranging from 0 to 200 µg/ml. The peptide-antibody mixtures were then added to the integrin-coated microwells. Following incubation at 37° C. for 2 hours, the plates were washed thoroughly, and bound CNTO95 was detected using peroxidase-conjugated goat anti-human IgG, Fc gamma fragment antibody (1:5,000 dilution), followed by substrate addition as above. EC50 value was determined by the concentration of competing synthetic peptide that resulted in half-maximal CNTO95 binding to integrins αVβ3 or αVβ5.

Figure 5A:
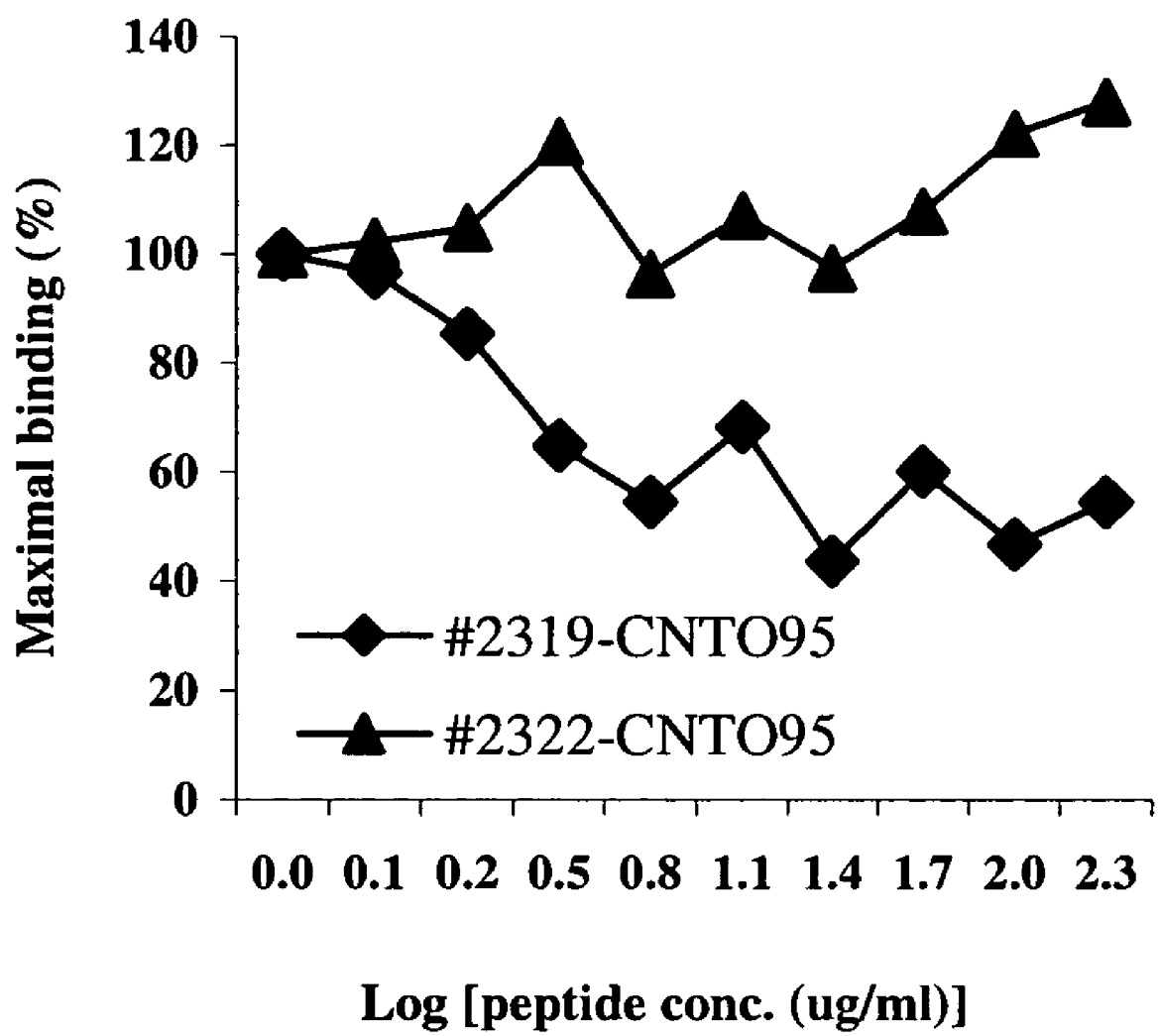
FIG. 5 contains graphs showing the results of ELISA assays demonstrating the concentration dependence of synthetic peptides binding to microtiter plates coated with alphaVbeta3 (A); and a graph showing the results of ELISA assays demonstrating the concentration dependence of synthetic peptides binding to microtiter plates coated with alphaVbeta5 (B).

CEN2319 and CEN 2322 synthetic peptides were analyzed for binding specificity using competitive ELISA on plates coated with various integrins. The data, shown in FIGS. 5A and 5B were used to calculate the EC50 for CEN2319 peptide to compete CNTO95 mAb binding to αVβ3 and which was determined to be 5.8 µM (FIG. 5A). On αVβ5-coated plates, CEN2319 alone showed significant inhibition of CNTO95 binding to integrin αVβ5. CEN2322 peptide did not compete with CNTO95 binding to αVβ3 or αVβ5.

Overall, the competitive ELISA data demonstrated that synthetic peptide CEN2319 inhibits CNTO95 mAb binding to integrins αVβ3 and αVβ5.

EXAMPLE 4

Binding Affinities and Stoichiometries of Synthetic Peptides for CNTO95

Titration microcalorimetry is a technique used to measure equilibrium binding affinity by monitoring the enthalpy of binding as a function of titrant added to second molecule at fixed temperature. To determine binding affinities and stoichiometries of synthetic peptides for CNTO95, titration calorimetry experiments were carried out with a Microcal (Amherst, Mass.) MCS isothermal titration calorimeter. Protein concentrations were measured by absorbance at 280 nm. Aliquots of peptide were titrated into a fixed concentration of CNTO95 at 3 µM in Dulbecco's PBS. Heats of binding are monitored with each injection. Peptides were added until the observed heats approach the heats of diluted peptides into buffer. Calorimetry data were analyzed with Microcal ORIGIN software according to a single-site binding model in each case (Wiseman et al., Anal. Biochem. 179: 131-137, 1989). The model includes an equilibrium binding constant (Kd), a molar binding enthalpy change (ΔH) and a molar binding ratio for the binding reaction at 25° C. Table 3 gives the calculated CNTO95 binding properties of synthetic peptides from titration calorimetry data.

TABLE 3

| Peptide | Molar ratio (Peptide/CNTO95) | ΔH (cal/mole) | Kd (µM) | Comments |
|---|---|---|---|---|
| CEN2319 | 2.2 | −12,000 | 4.2 | |
| CEN2322 | — | −325 | — | No binding |

Figure 6A:
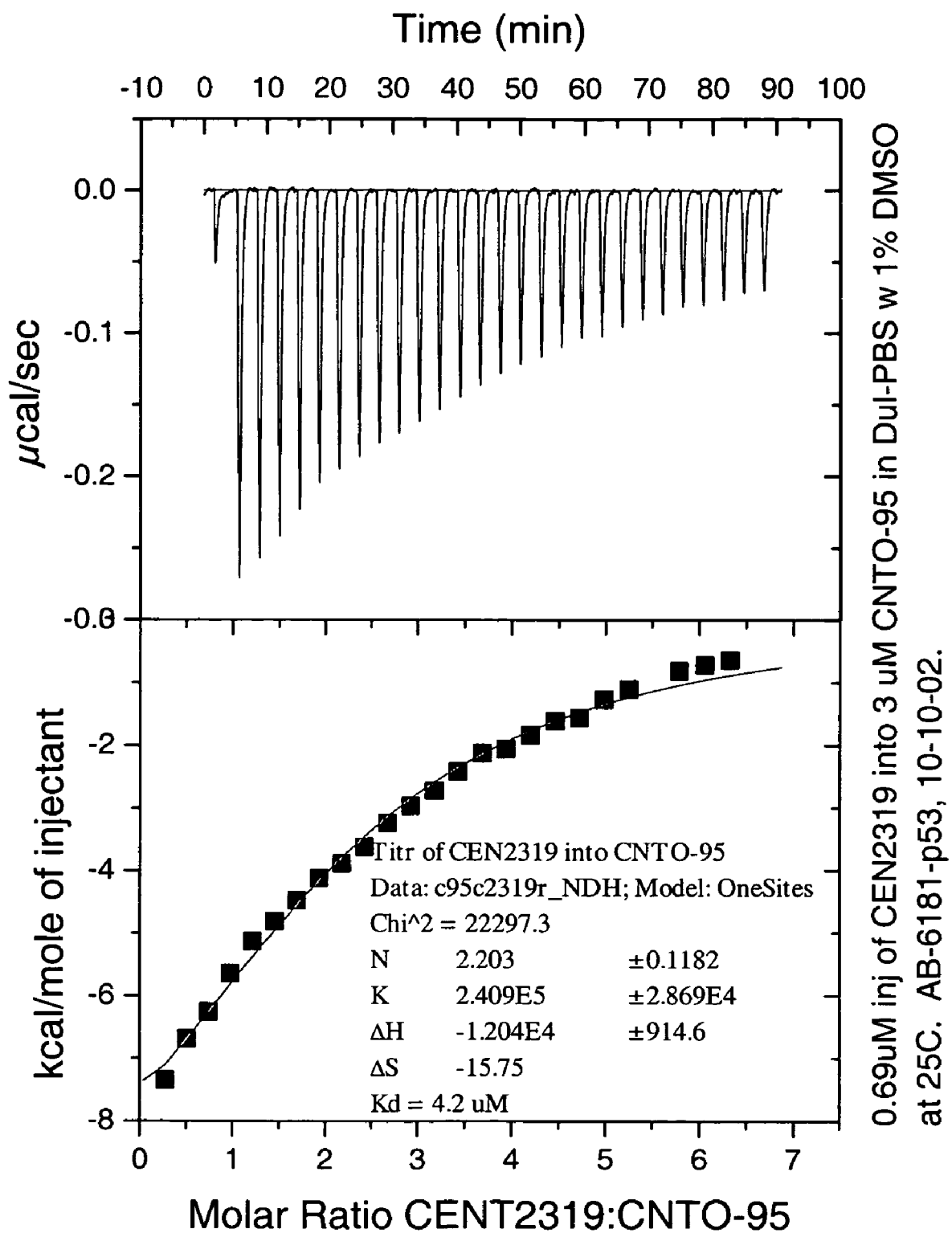
FIG. 6 are tracings and graphs showing the titration calorimetry data for CEN2319 peptide binding to CNTO95 mAb (A); and titration calorimetry data for CEN2322 peptide binding to CNTO95 mAb (B).

In this study, we have demonstrated that two synthetic CEN2319 peptides bind to one CNTO95 mAb and the binding affinity for CEN2319 peptide given as Kd value is 4.2 µM (FIG. 6A and Table 3).

EXAMPLE 5

Positional Substitution Analysis of Peptide CEN2319

In order to further understand the contribution of each amino acid residue in the binding, systematic substitution at each position were made and tested. The binding analysis was carried out by spotting the various peptides on a nitrocellulose membrane and probing with CNTO95 followed by HRP-conjugated goat-anti-human Fc antibody and color developed using a peroxidase substrate. The relative densities of color at each spot were then scored as given in Table 4 below.

TABLE 4

| | Position | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Original Residue | D | F | R | S | W | W | D | L | S | G | Y | R |
| A | | | +++ | | | | | | ++ | + | ++ | +++ |
| R | | | + | | | | | | ± | | ± | + |
| N | | | + | | | | | | +++ | + | + | ++ |
| D | + | | ++ | | | | ++ | | ± | ++ | ++ | +++ |
| C | | | | | | | | | | | | |
| Q | | | ++ | | | | | ± | ++ | ++ | ++ | ++ |
| E | | | + | | | | +++ | ± | ++ | +++ | +++ | +++ |
| G | | | ± | | | | | | ± | + | ++ | ++ |
| H | ± | ± | ± | | ± | ± | ± | ± | ++ | | ++ | ++ |
| I | | | ± | | | | | ++ | + | ± | + | ++ |
| L | | | +++ | | | | | ++ | ± | ± | + | ++ |
| K | | | ± | | | | | | | | | ± |
| M | | | ++ | | | | | ± | +++ | + | + | +++ |
| F | | + | ++ | | ++ | | | ± | ++ | + | ± | + |
| P | | | ± | | | | | | | ++ | ++ | ++ |
| S | | | +++ | + | | | | | + | + | + | ++ |
| T | | | + | | | | | ± | ++ | + | ++ | ++ |
| W | | | ± | | ++ | + | | | ± | + | + | + |
| Y | | ± | + | | +++ | | | ± | +++ | + | + | + |
| V | | | ± | | | | | ++ | ++ | + | ++ | ++ |
| Allowed Residues | D | F | X | S | Y/W/F | W | E/D | I/L/V | X | X | X | X |

Intensity:
+++: very strong;
++: strong;
+ equivalent;
±: weak;
Blank: negative.

These data show that the allowable positional substitutions are: an aromatic residue at position 5, a negative charge at position 7, and a hydrophobic residue at position 8. Substitutions at position 3 and 9-12 had no substantial effect, while any substitution at positions 1,2,4 and 6 dramatically reduced the binding of CNTO95 to the peptide.

EXAMPLE 6

Preparation of an Alternate Mimetope Peptide

Using the derived consensus formula (SEQ. ID. NO: 1):
DFXS----(Y/W/F)----W---(E/D)--------(I/L/V)----------$X_4$
DFXS---Aromatic---W-Negative charge--Hydrophobic-Optional Branched Chain an alternate antagonist peptide, CEN2553, having the sequence DFRSWWDLEE, (SEQ ID. NO: 5) was synthesized and tested for the ability to prevent CNTO95 from binding its target on the cell surface and by a functional assay. The C-terminal glutamate residues were added to increase overall solubility of the peptide only.

For the detection of surface integrins, A375.S2 cells (human melanoma cells) were harvested, rinsed, suspended in unsupplemented RPMI media. The antibody, CNTO95, was incubated at a final concentration of 10 ug/ml with or without peptides at the concentrations given in Table 1 for 1 hr. Then, the cell solution was added and incubated for an additonal 60 minutes on ice followed by addition of PE-labeled goat anti-human antibody IgG-Fc (10 ug/ml). Absence of primary antibody or substitution of primary antibody with isotype matched antibody served as negative controls. Cells were immediately analyzed with a FACS Scan II flow cytometer (Becton Dickinson, Mountain View, Calif.). The data was plotted as counts versus PE fluorescence and showed, in each case, a single distinct peak. For simplicity, the mean channel fluorescence for each peak was used as the relative staining value (Table 5). The results showed that competitive peptides selected from phage display and a modification based on the positional substitution analysis both inhibited CNTO 95 binding to cells.

TABLE 5

| PEPTIDE | Conc of Peptide (ug/ml) | Mean Channel Fluorescence |
|---|---|---|
| Cells Only | — | 3.36 |
| Cells + CNTO95 only | — | 89.7 |
| +CEN2319 | 100 | 12.27 |
| +CEN2319 | 200 | 11.60 |
| +CEN2322 | 100 | 90.55 |
| +CEN2322 | 200 | 92.40 |
| +CEN2553 | 100 | 12.95 |
| +CEN2553 | 200 | 9.41 |

Figure 7:
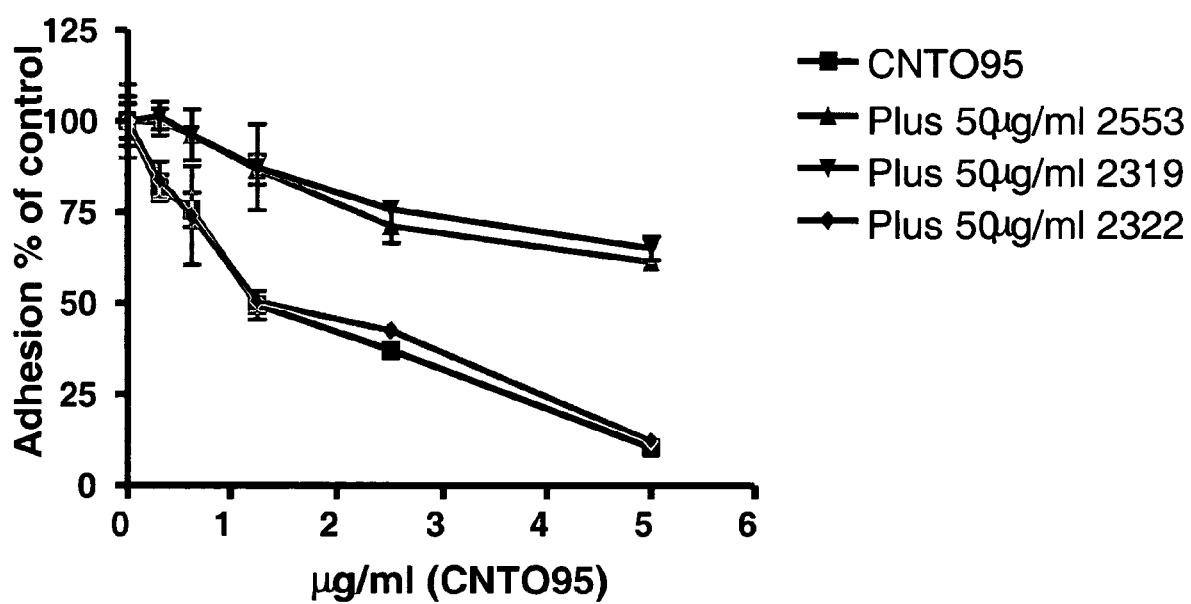
FIG. 7 is a graph showing the affect of CEN2319, CEN2553, the native peptide CEN 2322, on the inhibition of cellular adhesion by CNTO95 to vitronectin coated plates.

For cell adhesion assays, Microtiter plates (Linbro-Titertek, ICN Biomedicals, Inc) were coated at 4° C. overnight with vitronectin (1 mg/ml). Immediately before use plates were rinsed with PBS and blocked for 1 hour with 1% BSA/PBS (pH 7.4). Adherent cells (M21, human melanoma cells) were labeled with Calcein AM fluorescent dye (Molecular Probes, Eugene, Oreg.) according to the manufacturer's instructions, harvested, washed twice, and suspended in 0.1% BSA in DMEM medium. Various concentration of Antibodies were incubated with peptides for 1 hrs. Cell density was adjusted to $5\times10^5$/ml and they were incubated with antibody and peptide solution for 15 min at 37° C. The cell-antibody mixture was added to wells (100 μl per well) and incubated for 1 h at 37° C. Plates were rinsed twice with PBS to remove unbound cells and adhesion was measured in a fluorescence plate reader (Fluoroskan) at 485-538 nm. Cell adhesion to BSA-coated wells served as a negative control. Isotype matched antibodies served as a negative control. FIG. 7 shows that the effect of the 10-mer sequence (SEQ. ID. NO: 5) based on the derived formula (SEQ. ID. NO: 1) was indistinguishable from the peptide CEN2319 (SEQ. ID. NO: 2) isolated originally by capture of phage displaying the peptide by binding to CNTO95 directly.

SUMMARY

Figure 5B:
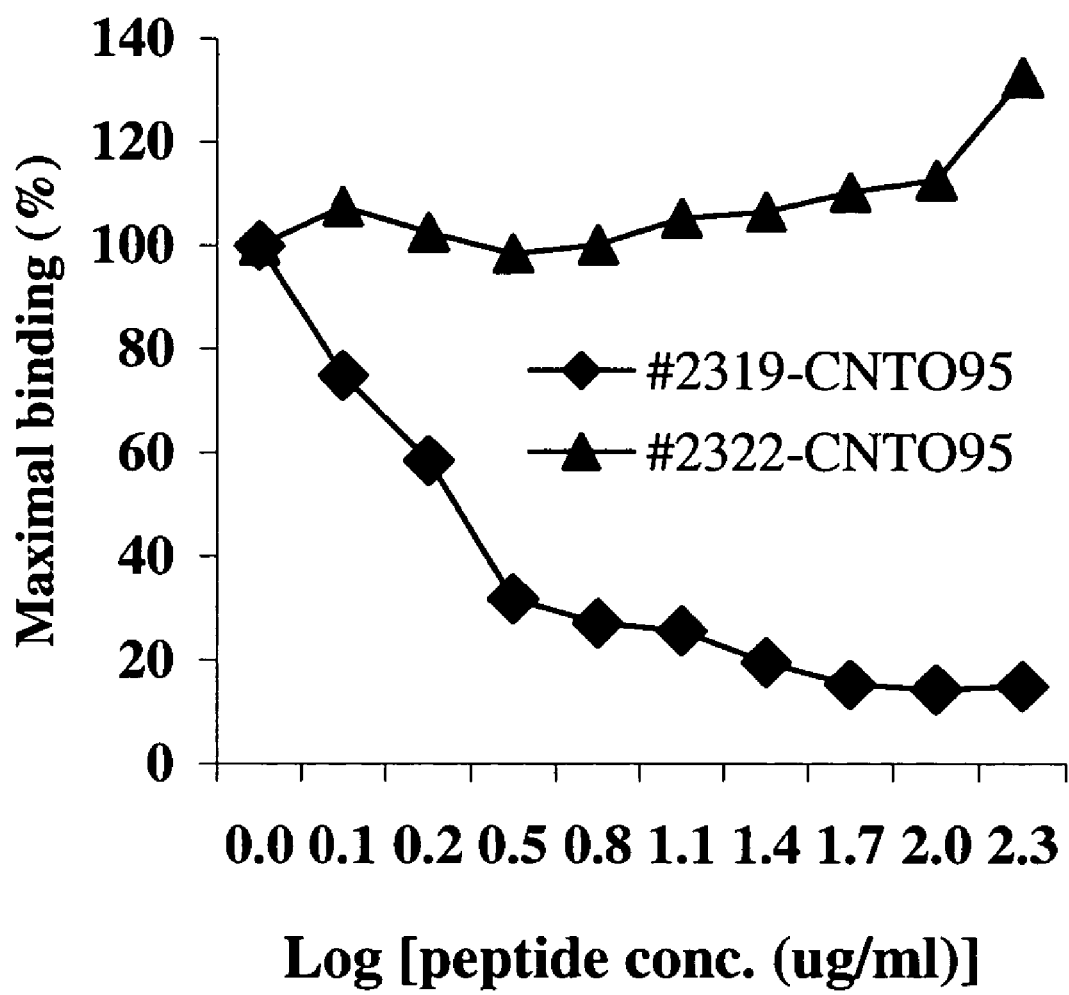
Figure 6B:
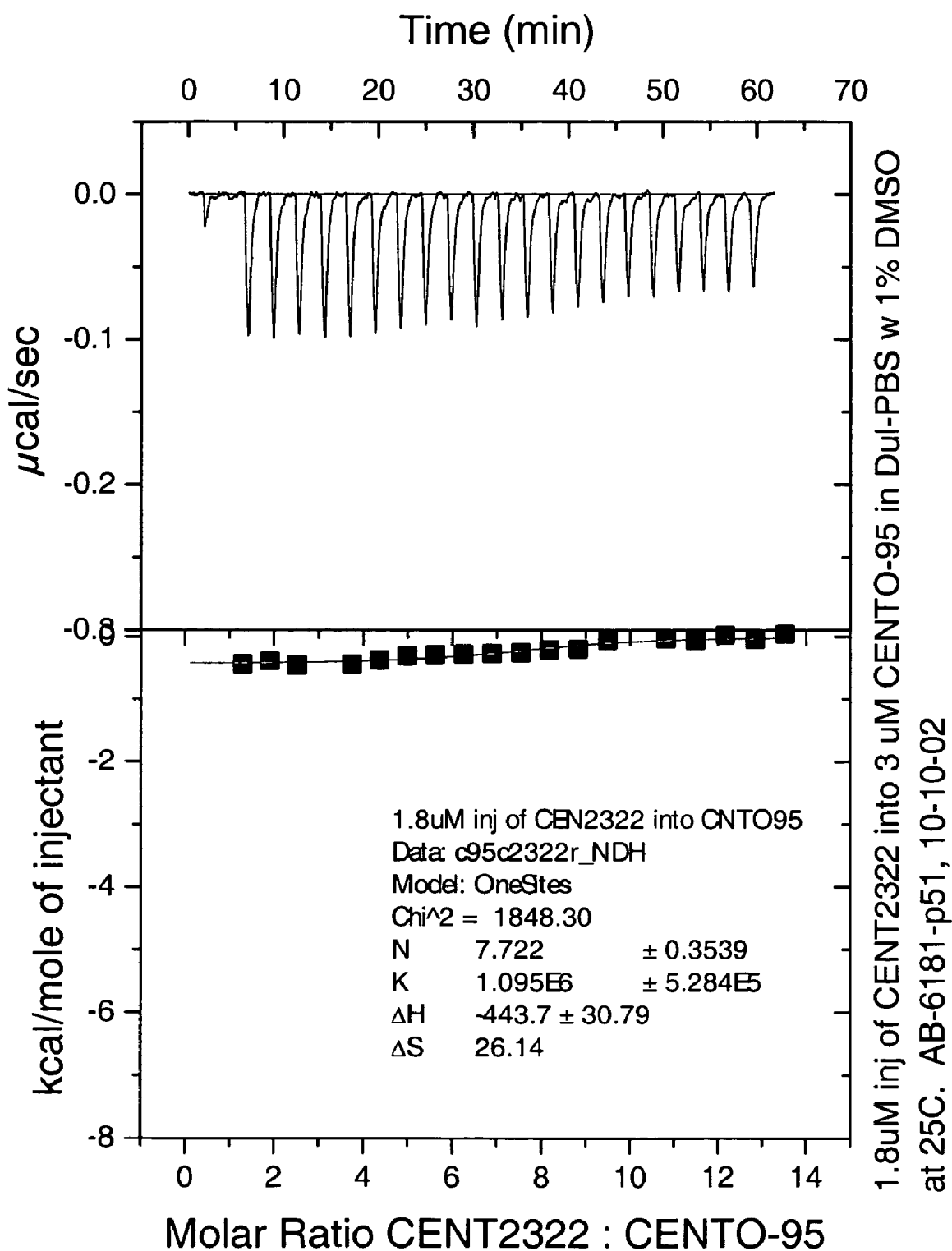

The equilibrium affinity Kd value, 4.2 µM, for CEN2319 peptide binding to CNTO95 was obtained by titration microcalorimetry (FIG. 6A and Table 3). There is no evidence for CEN2322 peptide binding to CNTO95 mAb (FIG. 6B and Table 3). These data were in good agreement with those obtained from competitive ELISA data (FIGS. 5A and 5B). Evidence for 2:1 stoichiometry for CEN2319 peptide to CNTO95 mAb using titration microcalorimetry (FIG. 6A) was also obtained. Molar binding ratio was determined by non-linear least squares analysis of the data in FIG. 6A and was given in Table 3. Deviation from theoretical 2.0 are likely due to the inherent errors in defining reactant concentrations by absorbance at 280 nm and weighing the mass of synthetic peptides. In this case, the molar binding ratio 2:1 for CEN2319 peptide to CNTO95 argues strongly that each Fab arm of CNTO95 mAb binds one peptide.

Using data from alignments of the binders and as compared to the parent sequence of the human alpha V integrin subunit, a formula was derived, which maps subregions of the binding surface necessary for the preparation of an antagonist peptide to the Mab CNTO95. The utility this formula was demonstrated as a peptide (SEQ. ID. NO. 5) conforming to the formula and which is one of the possible species included in the group described by SEQ. ID. NO: 1, was shown to behave identically to a selected binding antagonist.

What is to be claimed:

1. A peptide consisting of the amino acid sequence of the formula:

Asp Phe $Xaa_1$ Ser $Xaa_2$ Trp $Xaa_3$ $Xaa_4$ $Xaa_5$ $Xaa_6$ $Xaa_7$ $Xaa_8$, wherein $Xaa_2$ is selected from Trp, Tyr and Phe, $Xaa_3$ is selected from Glu and Asp, $Xaa_4$ is selected Ile, Leu and Val and $Xaa_1$, $Xaa_5$ $Xaa_6$ $Xaa_7$ $Xaa_8$ are independently selected from any naturally occurring amino acid (SEQ. ID. No.1).

2. A peptide according to claim 1 of the formula:

DFRSWWDLSGYR.        (SEQ. ID. No.2)

3. The peptide of the formula:

DFRSWWDLEE.          (SEQ. ID. No.5)

* * * * *

```
                         SEQUENCE LISTING

<160> NUMBER OF SEQ ID NOS: 5

<210> SEQ ID NO 1
<211> LENGTH: 12
<212> TYPE: PRT
<213> ORGANISM: Artificial Sequence
<220> FEATURE:
<223> OTHER INFORMATION: Consensus peptide based sequence from all
      binding peptides
<220> FEATURE:
<221> NAME/KEY: MISC_FEATURE
<222> LOCATION: (3)..(3)
<223> OTHER INFORMATION: Any naturally occuring amino acid
<220> FEATURE:
<221> NAME/KEY: MISC_FEATURE
<222> LOCATION: (5)..(5)
<223> OTHER INFORMATION: Trp or Tyr or Phe
<220> FEATURE:
<221> NAME/KEY: MISC_FEATURE
<222> LOCATION: (7)..(7)
<223> OTHER INFORMATION: Asp or Glu
<220> FEATURE:
<221> NAME/KEY: MISC_FEATURE
<222> LOCATION: (8)..(8)
<223> OTHER INFORMATION: Leu or Ile or Val
<220> FEATURE:
<221> NAME/KEY: MISC_FEATURE
<222> LOCATION: (9)..(12)
<223> OTHER INFORMATION: Any naturally occurring amino acid

<400> SEQUENCE: 1

Asp Phe Xaa Ser Xaa Trp Xaa Xaa Xaa Xaa Xaa Xaa
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Phage Library Derived Sequence

<400> SEQUENCE: 2

Asp Phe Arg Ser Trp Trp Asp Leu Ser Gly Tyr Arg
1               5                   10

<210> SEQ ID NO 3
<211> LENGTH: 7
```

```
-continued

<212> TYPE: PRT
<213> ORGANISM: Artificial Sequence
<220> FEATURE:
<223> OTHER INFORMATION: Phage Library Derived Sequence
<220> FEATURE:
<221> NAME/KEY: misc_feature
<222> LOCATION: (5)..(5)
<223> OTHER INFORMATION: Xaa can be any naturally occurring amino acid

<400> SEQUENCE: 3

Ser Pro Leu Phe Xaa Pro Trp
1               5

<210> SEQ ID NO 4
<211> LENGTH: 12
<212> TYPE: PRT
<213> ORGANISM: Homo sapiens
<220> FEATURE:
<221> NAME/KEY: PEPTIDE
<222> LOCATION: (1)..(12)
<223> OTHER INFORMATION: Residues 564 to 575 inclusive of human alpha V
      integrin subunit protein

<400> SEQUENCE: 4

Asp Tyr Arg Thr Ala Ala Asp Thr Thr Gly Leu Gln
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Phage Library Derived Sequence

<400> SEQUENCE: 5

Asp Phe Arg Ser Trp Trp Asp Leu Glu Glu
1               5                   10
```